(12) United States Patent
Ju et al.

(10) Patent No.: US 10,564,080 B2
(45) Date of Patent: Feb. 18, 2020

(54) METHOD FOR MEASURING STRESS FIELD VARIATIONS DURING $CO_2$ FRACTURING PROCESS

(71) Applicant: CHINA UNIVERSITY OF MINING AND TECHNOLOGY, BEIJING, Beijing (CN)

(72) Inventors: Yang Ju, Beijing (CN); Peng Liu, Beijing (CN); Hongbin Liu, Beijing (CN); Yongming Yang, Beijing (CN)

(73) Assignee: CHINA UNIVERSITY OF MINING AND TECHNOLOGY, BEIJING, Beijing (CN)

( * ) Notice: Subject to any disclaimer, the term of this patent is extended or adjusted under 35 U.S.C. 154(b) by 0 days.

(21) Appl. No.: 16/317,815

(22) PCT Filed: Apr. 17, 2018

(86) PCT No.: PCT/CN2018/083339
§ 371 (c)(1),
(2) Date: Jan. 14, 2019

(87) PCT Pub. No.: WO2018/192481
PCT Pub. Date: Oct. 25, 2018

(65) Prior Publication Data
US 2019/0360904 A1  Nov. 28, 2019

(30) Foreign Application Priority Data
Apr. 18, 2017 (CN) .......................... 2017 1 0252945
Apr. 18, 2017 (CN) ...................... 2017 2 0408794 U

(51) Int. Cl.
*G01N 3/00* (2006.01)
*G01N 3/12* (2006.01)
(Continued)

(52) U.S. Cl.
CPC ............. *G01N 3/12* (2013.01); *E21B 43/164* (2013.01); *E21B 49/006* (2013.01); *G06T 17/05* (2013.01);
(Continued)

(58) Field of Classification Search
CPC ............. G01N 3/12; G01N 2203/0044; G01N 2203/0066; G01N 2203/0256;
(Continued)

(56) References Cited

U.S. PATENT DOCUMENTS 7,730,951 B2 * 6/2010 Surjaatmadja ........ E21B 43/263
166/250.1
2004/0176911 A1 * 9/2004 Bratton .................... G01V 1/50
702/6
(Continued)

FOREIGN PATENT DOCUMENTS

CN 104655495 A 5/2015
CN 105181421 A 12/2015
(Continued)

OTHER PUBLICATIONS

International Search Report for PCT/CN2018/083339 dated Jul. 6, 2018, ISA/CN.
(Continued)

*Primary Examiner* — Max H Noori
(74) *Attorney, Agent, or Firm* — Yue (Robert) Xu; Apex Attorneys at Law, LLP

(57) ABSTRACT

A method for measuring a stress field evolution during a $CO_2$ fracturing process is provided, which is adopted to not only transparently display the spatial distribution and propagation morphology of internal fracturing fracture of a three-dimensional physical models, but also obtain internal three-dimensional stress phase diagram in a fracture propagation process by integration of a CT scanning, a digital recon-
(Continued)

struction, a 3D printing, a $CO_2$ fracturing experiment, a stress freezing and a photoelastic measurement techniques, thereby realizing transparent display and quantitative characterization of the three-dimensional stress field and its evolution law of a solid matter in the $CO_2$ fracturing process.

11 Claims, 5 Drawing Sheets

(51) Int. Cl.
*G06T 17/05* (2011.01)
*E21B 43/16* (2006.01)
*E21B 49/00* (2006.01)
*B33Y 80/00* (2015.01)
*B33Y 10/00* (2015.01)

(52) U.S. Cl.
CPC .............. *B33Y 10/00* (2014.12); *B33Y 80/00* (2014.12); *G01N 2203/0044* (2013.01); *G01N 2203/0066* (2013.01); *G01N 2203/0246* (2013.01); *G01N 2203/0256* (2013.01)

(58) Field of Classification Search
CPC .......... G01N 2203/0246; E21B 43/164; E21B 49/006; G06T 17/05; B33Y 10/00; B33Y 80/00
USPC .......................................................... 73/799
See application file for complete search history.

(56) References Cited

U.S. PATENT DOCUMENTS

| 2008/0083532 A1* | 4/2008 | Surjaatmadja | E21B 43/26 166/250.1 |
| 2015/0355158 A1* | 12/2015 | Lander | G01N 33/383 702/2 |

FOREIGN PATENT DOCUMENTS

| CN | 105608736 A | 5/2016 |
| CN | 105866000 A | 8/2016 |
| CN | 106182330 A | 12/2016 |
| CN | 207020004 U | 2/2018 |

OTHER PUBLICATIONS

Peng Liu et al, "Visual representation and characterization of three-dimensional hydrofracturing cracks within heterogeneous rock through 3D printing and transparent models", Int J Coal Sci Technol (2016) 3(3): pp. 284-294, Published with open access at Springerlink.com.

Yang Ju et al, "Visualization method of complex rock mass structure and stress field based on 3d printing technology", Science China Press, vol. 59, No. 32, Aug. 1, 2014, pp. 3109-3119.

* cited by examiner

METHOD FOR MEASURING STRESS FIELD VARIATIONS DURING $CO_2$ FRACTURING PROCESS

The present application is a national phase application of PCT international patent application PCT/CN2018/083339, filed on Apr. 17, 2018 which claims the priority to the Chinese patent application No. 201710252945.6 filed with the Chinese Patent Office on Apr. 18, 2017 and titled "METHOD FOR MEASURING STRESS FIELD EVOLUTION DURING CO2 FRACTURING PROCESS" and the priority to Chinese patent application No. 201720408794.4 filed with the Chinese Patent Office on Apr. 18, 2017 and titled "SYSTEM FOR MEASURING STRESS FIELD EVOLUTION DURING CO2 FRACTURING PROCESS", all of which are incorporated herein by reference in their entities.

FIELD

The disclosure relates to the technical field of internal stress field measurement, in particular to a method for measuring stress field evolution during a $CO_2$ fracturing process.

BACKGROUND

In a hydraulic fracturing process applied for an unconventional oil and gas, a large amount of water resources are consumed, and a large number of harmful additives contained in the fracturing fluid are prone to cause eco-environmental pollution. Consequently, a supercritical $CO_2$ fracturing becomes one type of waterless fracturing technology which currently has been a developing focus.

Due to the complexity of the $CO_2$ fracturing process, some of basic theory and method for the hydraulic fracturing are not fully applicable to a research on the supercritical $CO_2$ fracturing. The existing researches on a supercritical $CO_2$ mostly focus on the qualitative analysis of a fracture network structure formed after performing a $CO_2$ fracturing. However, it is impossible to observe and characterize the fracturing process.

In the conventional art, a quantitatively analysis on the distribution and evolution law of a stress field in the process of fracture expansion is conducted by a numerical simulation method. However, the computational precision of the numerical simulation method is prone to be affected by external conditions. Consequently, the accuracy and reliability of a numerical simulation result cannot be ensured.

SUMMARY

A method for measuring a stress field evolution during a $CO_2$ fracturing process is provided according to the present disclosure, to solve the problem in the conventional art that the accuracy and reliability of the numerical simulation result cannot be ensured because the computational precision is prone to be affected by external conditions.

For this purpose, a method for measuring a stress field evolution during a $CO_2$ fracturing process is provided in the present disclosure. The method includes:

performing, by a $CO_2$ pumping system, a $CO_2$ fracturing experiment on multiple identical and transparent three-dimensional physical models of actual reservoir cores;

performing, by a computer, a digital reconstruction on a CT scan result of the three-dimensional physical models on which the $CO_2$ fracturing experiment has been performed, to obtain a three-dimensional digital model with a complete fracture network, and clipping, by the computer, different fracture states in the three-dimensional digital model with the complete fracture network to generate three-dimensional digital models in different fracture states;

printing, by a 3D printer, multiple three-dimensional physical models in the different fracture states based on the three-dimensional digital models in the different fracture states;

performing, by the $CO_2$ pumping system, a $CO_2$ fracturing experiment on each of the three-dimensional physical models in the different fracture states under a target pressure corresponding to the three-dimensional physical model;

performing, by a thermo-controlled oven, a cooling process on each of the three-dimensional physical models on which the $CO_2$ fracturing experiment has been performed under the target pressure corresponding to the three-dimensional physical model;

slicing, by a slicer, each of the three-dimensional physical models on which the cooling process has been performed, to obtain three orthogonal plane two-dimensional slices of each of the three-dimensional physical models; and processing, by the computer, a stress fringe distribution to obtain a three-dimensional maximum shear stress at each point in each of the three-dimensional physical models, where the stress fringe distribution is obtained by performing a two-dimensional photoelastic experiment on the three orthogonal plane two-dimensional slices that meet experimental requirements.

Optionally, the different fracture states include a state before fracture initiation, a state that a fracture propagates to a preset length, and a state that a fracture arrests; and the clipping different fracture states in the three-dimensional digital model with the complete fracture network to generate three-dimensional digital models in different fracture states includes:

performing a region threshold segmentation, a clipping and a reconstruction on an image of the CT scan result by an image processing technology to obtain a three-dimensional digital model in the state that a fracture propagates to a preset length.

Optionally, the performing, by the $CO_2$ pumping system, a $CO_2$ fracturing experiment on each of the three-dimensional physical models in the different fracture states under a target pressure corresponding to the three-dimensional physical model includes:

injecting, by the $CO_2$ pumping system, a supercritical $CO_2$ into a three-dimensional physical model in the state before fracture initiation, and stopping injecting the supercritical $CO_2$ and maintaining a current injecting pressure when the injecting pressure is lower than a breakdown pressure by a preset pressure difference; and injecting, by the $CO_2$ pumping system, a supercritical $CO_2$ into a three-dimensional physical model in the state that a fracture propagates to a preset length, and stopping injecting the supercritical $CO_2$ and maintaining a current injecting pressure when the injecting pressure is lower than a pressure at which a current fracture is formed by a preset pressure difference.

Optionally, before the performing, by a $CO_2$ pumping system, a $CO_2$ fracturing experiment on multiple identical and transparent three-dimensional physical models of actual reservoir cores, the method further includes:

performing, by the computer, a digital reconstruction on a scan result of the actual reservoir cores to obtain a three-dimensional digital model of the actual reservoir cores;

printing, by the 3D printer, the multiple identical and transparent three-dimensional physical models of the actual reservoir cores based on the three-dimensional digital model of the actual reservoir cores;

processing, by the thermo-controlled oven, the multiple three-dimensional physical models of the actual reservoir cores to make properties of the multiple three-dimensional physical models of the actual reservoir cores stable; and applying, by a tri-axial loading device, a three direction servo loading on the multiple three-dimensional physical models of the actual reservoir cores until a target value is reached.

Optionally, before performing, by the $CO_2$ pumping system, a $CO_2$ fracturing experiment on each of the three-dimensional physical models in the different fracture states under a target pressure corresponding to the three-dimensional physical model, the method further includes:

processing, by the thermo-controlled oven, the three-dimensional physical models in the different fracture states to make properties of the three-dimensional physical models in different fracture states stable; and applying, by a tri-axial loading device, a three direction servo loading on the three-dimensional physical models in the different fracture states until a target value is reached.

Optionally, the processing, by a thermo-controlled oven, the multiple three-dimensional physical models of the actual reservoir cores to make properties of the multiple three-dimensional physical models of the actual reservoir cores stable includes:

slowly heating, by the thermo-controlled oven, the multiple three-dimensional physical models of the actual reservoir cores to 60° C., and maintaining, by the thermo-controlled oven, the temperature for one hour to make the properties of the multiple the three-dimensional physical models of the actual reservoir cores stable.

Optionally, the processing, by a thermo-controlled oven, the three-dimensional physical models in the different fracture states to make properties of the three-dimensional physical models in the different fracture states stable includes:

slowly heating, by the thermo-controlled oven, the three-dimensional physical models in the different fracture states to 60° C., and maintaining, by the thermo-controlled oven, the temperature for one hour to make the properties of the three-dimensional physical models in the different fracture states stable.

Optionally, before the performing, by a $CO_2$ pumping system, a $CO_2$ fracturing experiment on three-dimensional physical models of actual reservoir cores, the method further includes:

adjusting, by a temperature control system of the $CO_2$ pumping system, an injecting pressure and a temperature of $CO_2$.

Optionally, the performing, by a thermo-controlled oven, a cooling process on each of the three-dimensional physical models on which the $CO_2$ fracturing experiment has been performed under the target pressure corresponding to the three-dimensional physical model includes:

setting a cooling speed of the thermo-controlled oven to be 2° C./h to make the temperate decline to an ambient temperature.

Optionally, the processing, by the computer, a stress fringe distribution to obtain a three-dimensional maximum shear stress at each point in each of the three-dimensional physical models includes:

performing, by the computer, a phase-shifting extraction based on the stress fringe distribution to obtain a stress field;

calculating, by the computer, a maximum shear stress distribution $(\tau_{max})_{xy}$, $(\tau_{max})_{yz}$ and $(\tau_{max})_{zx}$ in three orthogonal planes under a load according to a formula $\tau_{max}=\sqrt{(\tau_{max})_{xy}^2+(\tau_{max})_{yz}^2+(\tau_{max})_{zx}^2}$; and calculating, by the computer, the three-dimensional maximum shear stress at each point in the three-dimensional physical model based on the maximum shear stress distribution $(\tau_{max})_{xy}$, $(\tau_{max})_{yz}$ and $(\tau_{max})_{zx}$ in the three orthogonal planes.

A method for measuring a stress field evolution during a $CO_2$ fracturing process is further provided in the present disclosure. The method includes:

obtaining transparent three-dimensional physical models of a complex rock mass by a 3D printing technology;

recording distribution characteristics of three-dimensional stress fields in different fracture states by a frozen experiment using the three-dimensional physical models; and quantitatively visualizing and analyzing a distribution of each of the three-dimensional stress fields based on a photoelastic experiment and a phase shift analysis.

Optionally, the obtaining transparent three-dimensional physical models of a complex rock mass by a 3D printing technology includes:

printing, by a 3D printer, multiple identical three-dimensional physical models based on a three-dimensional digital model of an actual rock core, where the three-dimensional digital model is obtained by performing a CT scanning, an image processing and a three-dimensional reconstructing on the actual rock core.

Optionally, the recording distribution characteristics of three-dimensional stress fields in different fracture states by a frozen experiment using the three-dimensional physical models includes:

heating, by a heating device, a three-dimensional physical model which is selected from the three-dimensional physical models to make the selected three-dimensional physical model achieve a freezing temperature;

loading, by a tri-axial loading device, the three-dimensional physical model at the freezing temperature to simulate an in-situ stress state of a rock in the fracturing process;

performing, by a $CO_2$ pumping system, a $CO_2$ fracturing experiment on the loaded three-dimensional physical model to cause the loaded three-dimensional physical model to be in a specific fracture state in the fracturing experiment;

performing, by a thermo-controlled oven, a cooling process on the three-dimensional physical model in the specific fracture state; and repeating above operations to obtain distribution characteristics of stress fields of the three-dimensional physical models in different fracture states.

Optionally, the specific fracture state includes a state before fracture initiation, a state that a fracture propagates to a preset length, and a state that a fracture arrests.

Optionally, the quantitatively visualizing and analyzing a distribution of each of the three-dimensional stress fields based on a photoelastic experiment and a phase shift analysis includes:

slicing, by a slicer, each of the three-dimensional physical models in different fracture states on which a cooling process has been performed, to obtain three orthogonal plane two-dimensional slices of each of the three-dimensional physical models;

performing, by a photoelastic stress test system, a photoelastic analysis experiment on each of the orthogonal plane two-dimensional slices to obtain a photoelastic fringe pattern for each slice;

obtaining, by a computer, a distribution of a principal stress direction angle $\theta_u$ in a full field through a four-step color phase shift method, $$\theta = \frac{\pi}{8} - 0.25\tan\left[\frac{I_1 - I_3}{I_2 - I_4}\right],$$

and $\sin \delta \neq 0$, where $l_i$ is an intensity of an incident light;

obtaining an isochromatics phase diagram $\delta_u$ through an improved six-step phase shift method, $$\delta = \tan^{-1}\left[\frac{(I_5 - I_3)\sin 2\theta_u + (I_4 - I_6)\cos 2\theta_u}{I_1 - I_2}\right]$$

where $\begin{cases} I_5 - I_3 = -I_a \sin\delta \sin 2\theta, \\ I_4 - I_6 = -I_a \sin\delta \cos 2\theta, \\ I_1 - I_2 = -I_a \cos\delta \end{cases}$ $l_a$ is a modulation light intensity; and calculating a distribution of the stress field of the full field, $$\tau = \frac{\delta_u f_\sigma}{4\pi h}\sin 2\theta_u, (\sigma_x)_j = (\sigma_x)_i - \int_i^j \frac{\partial \tau_{xy}}{\partial y} dx$$

where $f_o$ is a fringe value of the model, and h is a thickness of the model;

synthesizing stress components in three orthogonal planes to obtain the distribution of the three-dimensional stress field at each point in the three-dimensional physical model.

Optionally, before the recording distribution characteristics of three-dimensional stress fields in different fracture states by a frozen experiment of the three-dimensional physical models, the method further includes:

changing a phase of a $CO_2$ gas by adjusting a pressure and a temperature of the gas in a $CO_2$ pumping system to ensure that a fracturing fluid is in a specific gas state or a supercritical state.

Optionally, the $CO_2$ pumping system includes a temperature control system configured to adjust an injecting pressure and a temperature of $CO_2$.

In the method for measuring the stress field evolution during the $CO_2$ fracturing process provided by the present disclosure, a $CO_2$ pumping system performs a $CO_2$ fracturing experiment on multiple identical and transparent three-dimensional physical models of actual reservoir cores; a computer performs a digital reconstruction on a CT scan result of the three-dimensional physical models on which the $CO_2$ fracturing experiment has been performed, to obtain a three-dimensional digital model with a complete fracture network, and clips different fracture states in the three-dimensional digital model with the complete fracture network to generate three-dimensional digital models in different fracture states; a 3D printer prints multiple three-dimensional physical models in the different fracture states based on the three-dimensional digital models in the different fracture states; the $CO_2$ pumping system performs a $CO_2$ fracturing experiment on each of the three-dimensional physical models in the different fracture states under a target pressure corresponding to the three-dimensional physical model; a thermo-controlled oven performs a cooling process on each of the three-dimensional physical models on which the $CO_2$ fracturing experiment has been performed under the target pressure corresponding to the three-dimensional physical model; a slicer slices each of the three-dimensional physical models on which the cooling process has been performed, to obtain three orthogonal plane two-dimensional slices of each of the three-dimensional physical models; and the computer processes a stress fringe distribution to obtain a three-dimensional maximum shear stress at each point in each of the three-dimensional physical models. That is, unlike the numerical simulation method in the conventional art, the method for measuring a stress field evolution during a $CO_2$ fracturing process according to the present disclosure is adapted to not only visually display the different fracture states of the three-dimensional physical model, but also quantitatively record the internal stress phase diagram of the three-dimensional physical model to realize the visualization and quantitative characterization of distribution of the three-dimensional stress field by integration of a digital reconstruction, a 3D printing technology, a $CO_2$ fracturing experiment, a temperature control and a two-dimensional photoelastic experiment. In addition, a complex structure of a discontinuous structure body is truly reflected, and the accuracy and reliability of the measurement result can be ensured by simultaneously performing the experiment described above on multiple identical and transparent three-dimensional physical models, Therefore, a problem in the conventional art, that the accuracy and reliability of the numerical simulation result cannot be ensured because the computational precision is prone to be affected by external conditions, can be avoided.

BRIEF DESCRIPTION OF THE DRAWINGS

For more clearly illustrating the embodiments of the present disclosure or the technical solutions in the conventional art, the drawings used when describing the embodiments or the conventional art will be briefly described hereinafter. Apparently, the drawings in the following description show only some embodiments of the present disclosure, and for an ordinary person skilled in the art, other drawings may be obtained based on the provided drawings without any creative work.

DETAILED DESCRIPTION OF THE EMBODIMENTS

The technical solutions in the embodiments of the present disclosure will be described clearly and completely hereinafter in conjunction with the drawings in the embodiments of the present disclosure. Apparently, the described embodiments are only a part of the embodiments of the present disclosure, rather than all embodiments. Other embodiments obtained by the person skilled in the art without any creative efforts based on the embodiments of the present disclosure should fall into the protection scope of the present disclosure.

A method for measuring a stress field evolution during a $CO_2$ fracturing process is provided in the present disclosure, to solve the problem in the conventional art that the accuracy and reliability of the numerical simulation result cannot be ensured because the computational precision is prone to be affected by external conditions.

Figure 1:
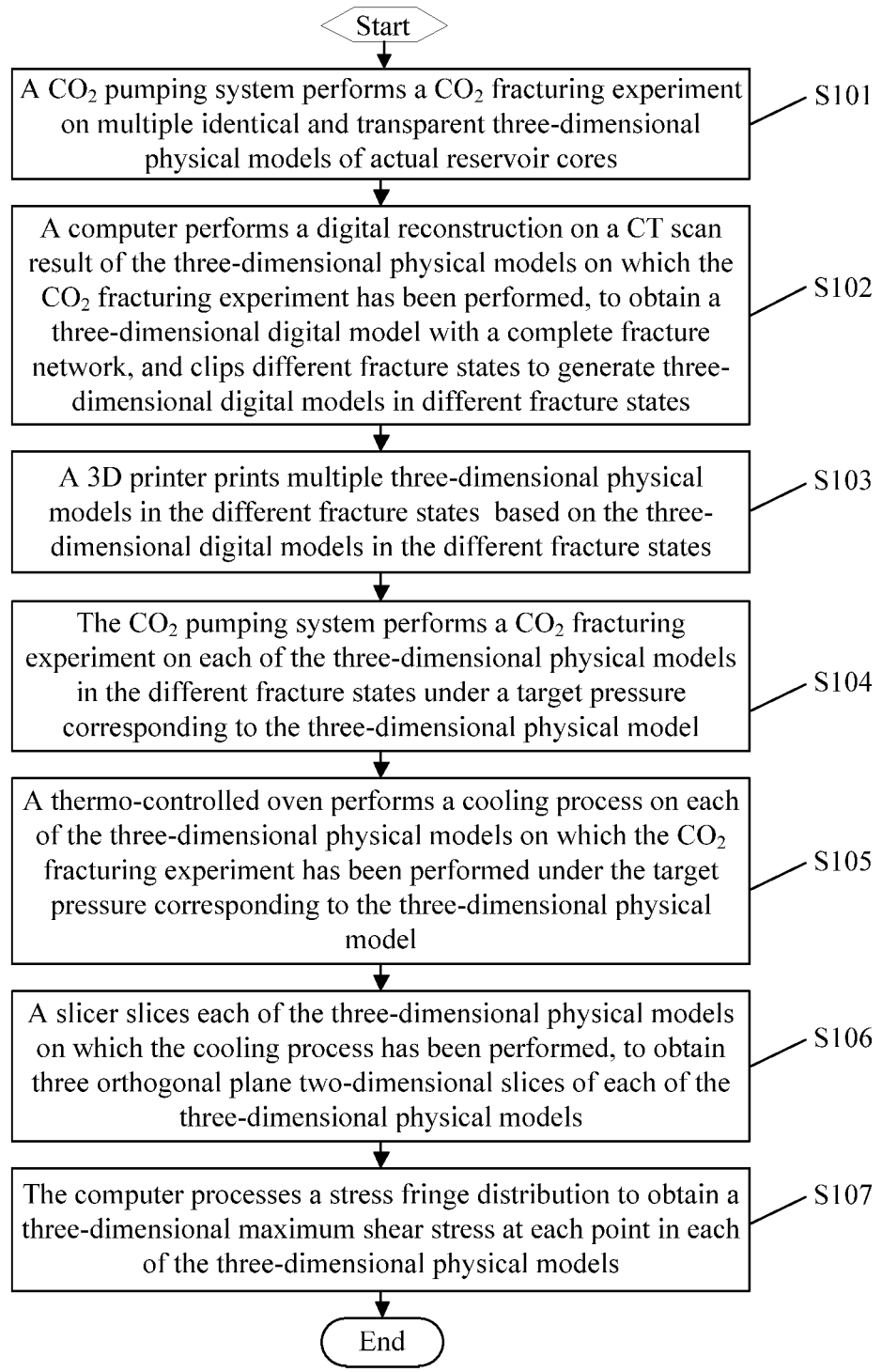
FIG. 1 is a flowchart of a method for measuring a stress field evolution during a $CO_2$ fracturing process according to an embodiment of the present disclosure.

Specifically, as shown in FIG. 1, the method for measuring the stress field evolution during the $CO_2$ fracturing process includes the followings steps S101 to S107.

In step S101, a $CO_2$ pumping system performs a $CO_2$ fracturing experiment on multiple identical and transparent three-dimensional physical models of actual reservoir cores. That is, the $CO_2$ pumping system performs the $CO_2$ fracturing experiment on multiple identical and transparent three-dimensional physical models that are similar in nature to actual reservoir cores.

Specifically, before the $CO_2$ is injected, a phase of the $CO_2$ gas may be changed by adjusting a pressure and a temperature of a gas to ensure that a fracturing fluid is in a specific gas state or a supercritical state.

That is, preferably, the $CO_2$ pumping system includes a temperature control system configured to adjust the injecting pressure and temperature of the $CO_2$.

Before the $CO_2$ fracturing experiment is performed, a tri-axial loading device is used to fix and load each of the three-dimensional physical models of the actual reservoir cores. After each of the three-dimensional physical models of the actual reservoir cores is fractured, it is stopped injecting the supercritical $CO_2$, the external three direction stress of the tri-axial loading device is unloaded, and each of the three-dimensional physical models of the actual reservoir cores is taken out from the thermo-controlled oven.

In step S102, a computer performs a digital reconstruction on a CT scan result of the three-dimensional physical models on which the $CO_2$ fracturing experiment has been performed, to obtain a three-dimensional digital model with a complete fracture network, and the computer clips different fracture states in the three-dimensional digital model with the complete fracture network to generate three-dimensional digital models in different fracture states.

In practice, a complete fracturing process may include three different fracture propagation stages, i.e., different fracture states, including: a state before fracture initiation, a state that a fracture propagates to a preset length, and a state that a fracture arrests. The fracture morphology at different fracturing stages are clipped from the reconstructed module with the complete fracture network.

Preferably, the clipping different fracture states in the three-dimensional digital model with the complete fracture network to generate three-dimensional digital models in different fracture states includes: performing a region threshold segmentation, a clipping and a reconstruction on an image of the CT scan result by an image processing technology to obtain a three-dimensional digital model in the state that a fracture propagates to a preset length.

The preset length may depend on a specific application environment, which is not limited herein, and all the lengths fall within the protection scope of the present disclosure.

In step S103, a 3D printer prints multiple three-dimensional physical models in the different fracture states based on the three-dimensional digital models in different fracture states.

According to the different fracture states above, 3D printing technology is used to reconstruct physical models to obtain different physical models staying at three different stages during the fracture propagation. i.e., a complete model with no pre-existing fracture, a model with a pre-existing fracture of a certain length, and a physical model after the fracture arresting.

In step S104, the $CO_2$ pumping system performs a $CO_2$ fracturing experiment on each of the three-dimensional physical models in the different fracture states under a target pressure corresponding to the three-dimensional physical model.

It is noteworthy that a second $CO_2$ fracturing (i.e., a secondary fracturing) experiment in step S104 is not a repetition of a first $CO_2$ fracturing (i.e., a primary fracturing) experiment in step S101. The first $CO_2$ fracturing experiment in step S101 aims to obtain a final fracture network morphology of multiple identical and transparent three-dimensional physical models of actual reservoir cores under specific temperature and stress conditions.

As can be seen from above, the $CO_2$ fracturing actually experiences different initiation and propagation processes, consequently, forming a complete fracturing fracture network. In order to study the stress field evolution at the fracturing fracture tip of different fracture propagation stages, it is required to divide the complete fracture network obtained from the first $CO_2$ fracturing experiment into different propagation stages by step S102. That is, a dynamic fracture propagation process is decomposed into different quasi-static fracture propagation stages. The three-dimensional digital models with certain fracture lengths in different fracture propagation stages are clipped and reconstructed based on image processing technique. Moreover, by the 3D printing technology in step S103, printing and obtaining corresponding three-dimensional physical models. Thus the second $CO_2$ fracturing experiment can be performed according to step S104 based on the three-dimensional physical models in different stages, as well as carries out the stress frozen experiments by maintain the corresponding injecting pressure stable. As a result, visualizing and quantitatively characterizing of the three-dimensional stress field during CO2 fracturing process may be realized.

Specifically, different target pressures may be set for three-dimensional physical models in different fracture states. Preferably, the pressure may be set as follows.

The $CO_2$ pumping system injects a supercritical $CO_2$ into a three-dimensional physical model, and maintains the injecting pressure when the injecting pressure is lower than a breakdown pressure by a preset pressure difference.

The $CO_2$ pumping system injects a supercritical $CO_2$ into a three-dimensional physical model with a fracture propagating to a preset length, and maintains the injecting pressure when the injecting pressure is lower than a pressure at which a current fracture is formed by a preset pressure difference. The pressure at which the current fracture is formed is a pressure that could keep the fracture propagate forward.

The preset pressure difference may depend on a specific application environment, which is not limited herein, and all the pressure differences fall within the protection scope of the present disclosure.

The breakdown pressure in the fracturing process refers to the pressure at which the fracture emerges, that is, the peak point of the injecting pressure-time curve in a complete fracturing process. Once the injecting pressure exceeds the breakdown pressure, the fracture begins to initiate and propagate, to make the specimen (i.e., the three-dimensional physical model on which the experiment is performed) failed. In this step, the injecting pressure for the three-dimensional physical model in the state before fracture initiation is lower than the breakdown pressure obtained from the first fracturing process, for the fact that in order to perform the stress frozen experiment, it is necessary to ensure the three-dimensional physical model stay at an imminent fracturing state.

Except for the first $CO_2$ fracturing experiment, the subsequent $CO_2$ fracturing experiment is performed to achieve stress freezing, so it is required to ensure that the injecting pressure and an external confining pressure are maintained at a certain value without causing the fracture to continue to propagate. Therefore, the injecting pressure of the subsequent $CO_2$ fracturing experiment is based on the stress value in the pressure-time curve obtained by the first $CO_2$ fracturing experiment, ensuring that the applied injecting pressure is lower than the driving pressure required to cause the fracture to continue to propagate.

In step S105, a thermo-controlled oven performs a cooling process on each of the three-dimensional physical models on which the $CO_2$ fracturing experiment has been performed under the target pressure corresponding to the three-dimensional physical model.

Preferably, the cooling speed, setting on the thermo-controlled oven, may be 2° C./h to make the temperate decline to the ambient temperate.

Then, the external three direction stress of the tri-axial loading device may be unloaded, and each of the three-dimensional physical models on which the $CO_2$ fracturing experiment has been performed under the target pressure corresponding to the three-dimensional physical model is taken out from the thermo-controlled oven.

In step S106, a slicer slices each of the three-dimensional physical models on which the cooling process has been performed, to obtain three orthogonal plane two-dimensional slices of each of the three-dimensional physical models. Specifically, three three-dimensional physical models on which the cooling process has been performed may be selected, and may be sliced along three orthogonal planes x-y, y-z, and z-x to obtain three orthogonal plane two-dimensional slices of the three-dimensional physical models, and the slice has a thickness of 1 mm.

In step S107, a stress fringe distribution is processes by the computer to obtain a three-dimensional maximum shear stress at each point in each of the three-dimensional physical models.

The stress fringe distribution is obtained by performing a two-dimensional photoelastic experiment on the three orthogonal plane two-dimensional slices that meet experimental requirements.

In the specific practical application, firstly the three orthogonal plane two-dimensional slices are smoothed and polished to make them meet the experimental requirements, thus, these slices are used to carry out the two-dimensional photoelastic experiment to capture the stress fringe distribution. Furthermore, a three-dimensional maximum shear stress at each point in the three-dimensional physical model is obtained by step S107.

Unlike the existing method for displaying the evolution of the fracturing stress field using a numerical simulation, the method for measuring the stress field evolution in the $CO_2$ fracturing process provided by the embodiment is adopted to not only transparently display the spatial distribution and propagation morphology of internal fracturing fracture of a three-dimensional physical models, but also obtain internal three-dimensional stress phase diagram in a fracture propagation process by integration of a CT scanning, a digital reconstruction, a 3D printing, a $CO_2$ fracturing experiment, a stress freezing and a photoelastic measurement techniques, thereby realizing transparent display and quantitative characterization of the three-dimensional stress field and its evolution law of a solid matter in the $CO_2$ fracturing process. In addition, in the present embodiment, not only the complex discontinuous structure inside the solid matter can be truly reflected, but also the transparent analysis and characterization of the internal stress field and its evolution can be realized by using multiple identical and transparent three-dimensional physical photoelastic models, thereby ensuring the accuracy and reliability of the measurement results. Therefore, the problems, that the precision and accuracy of fracture expansion calculation cannot be ensured, the model with a complex structure is difficult to prepare and stress field in the fracture expansion cannot be continuously and transparently characterized, existed in the existing numerical simulation method and the traditional stress experiment technology are solved.

In one embodiment of the disclosure, a method of measuring stress field evolution during a $CO_2$ fracturing process is provide, the method includes steps (I) to (VI).

In step (I), multiple transparent three-dimensional physical models of complex rock masses are obtained. The 3D printer performs a printing according to a three-dimensional digital model of an actual rock core to obtain multiple identical three-dimensional physical models. The three-dimensional digital model is obtained by performing a CT scanning, an image processing, and a three-dimensional reconstructing on the actual rock core.

In step (II), a supercritical $CO_2$ is prepared. A phase of the $CO_2$ gas is changed by adjusting a pressure and a temperature of a gas in the $CO_2$ pumping system to ensure that a fracturing fluid is in a specific gas state or a supercritical state. Preferably, the $CO_2$ pumping system includes a temperature control system configured to adjust an injecting pressure and a temperature of the $CO_2$.

In step (III), in a $CO_2$ fracturing stress visualization system, a stress frozen experiment using the three-dimensional physical model is performed to record the three-dimensional stress field characteristics of different fracture stages, that is, to record the model strain or deformation that can reflect the true stress field distribution.

Figure 4:
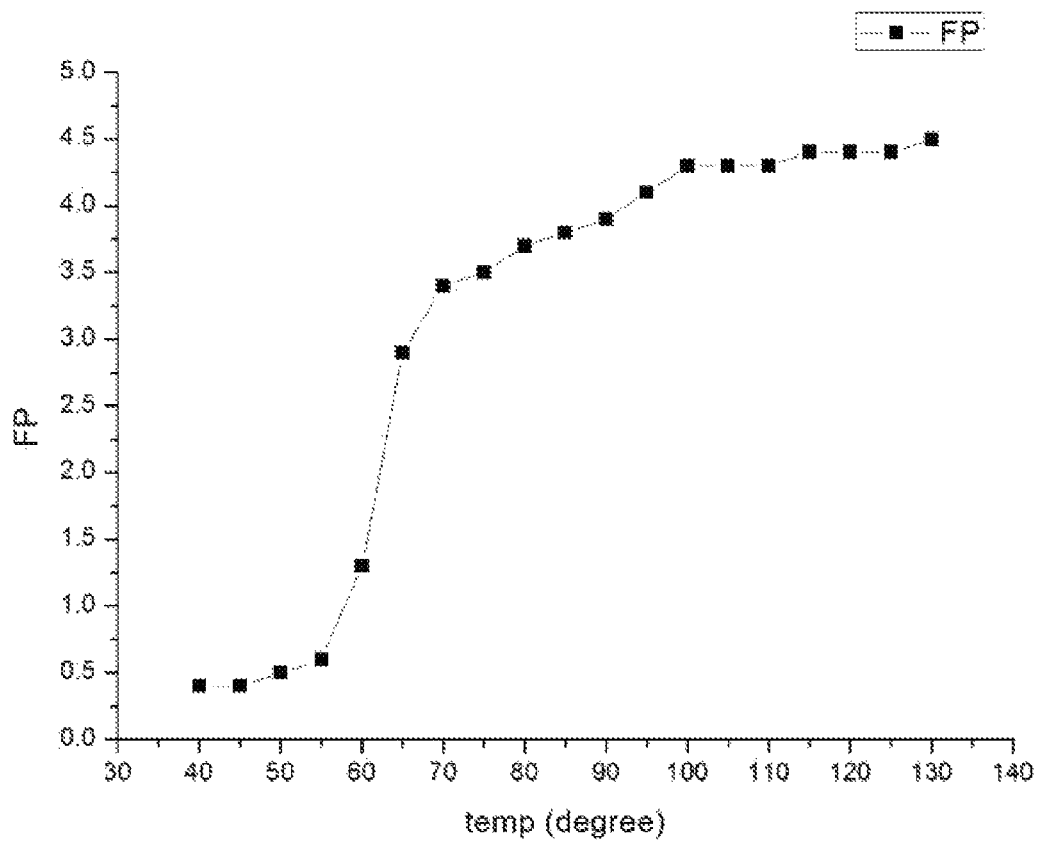
FIG. 4 is a thermo-optic curve diagram according to another embodiment of the present disclosure.

1. A freezing temperature of the three-dimensional physical models is reached by heating up, namely, the to-be-tested model in the multiple three-dimensional physical models are heated up by a thermo-controlled oven in the visualization system to the freezing temperature of the model. Preferably, 60° C. is served as the freezing temperature of each of the three-dimensional physical models. In practice, other temperatures may also be available, which are not limited herein. For the specific values, reference may be made to the thermo-optic curve of the three-dimensional physical model as shown in FIG. 4, and the thermo-optic curve is generally obtained by recording the change in the number of fringe order of a circular-disk under diametrical compression at different temperatures.

2. External three direction stress is loaded on the model, namely, the three-dimensional physical model is loaded by a tri-axial loading device until a preset target pressure is reached. The target pressure is the pressure withstood by a rock in an in-situ stress state in the fracturing process. Preferably, the in-situ stress state that the reservoir rock buried in a depth of 1000 m to 3000 m withstands may be selected. And in practice, the in-situ stress state that rocks buried in other depth withstands may be used, which is not limited herein.

3. A supercritical $CO_2$ is injected to perform the fracturing experiment, namely, a $CO_2$ pumping system performs a $CO_2$ fracturing experiment on the three-dimensional physical models. A value of the injecting pressure is controlled by accurate control of volume of the injected gas, to ensure that the physical models can be in different fracturing stages in the fracturing experiment, such as a stage before fracture initiation, a stage of stable propagation of fracture to a preset length.

Here, the fracturing experiment in which the model is in the state before fracture initiation means that the $CO_2$ pumping system injects a supercritical $CO_2$ into the three-dimensional physical model which has been heated and loaded as mentioned until the injecting pressure is slightly lower than a breakdown pressure of the model, thus maintains the injecting pressure stable.

Here, the fracture experiment in which the fracture propagates to a specific stage means that the $CO_2$ pumping system injects a supercritical $CO_2$ into the three-dimensional physical model above on which the heating and loading have been performed until the model fractures, and the injecting pressure is maintained constant and the pressure is lower than a pressure which drives the fracture to continue to propagate when the fracture propagates to a preset length. The stage of fracture expansion to a specific stage can depend on a specific application environment, which is not limited herein, and all fall within the protection scope of the present disclosure.

4. A thermo-controlled oven performs the cooling process on the model on which the above fracturing experiment has been performed, namely, the thermo-controlled oven controls the temperature of model to be slowly lowered from the freezing temperature to ambient temperature. Preferably, the model can be cooled to ambient temperature at a speed of 2° C./h. In practice, other cooling rates can also available, and are not limited herein. The $CO_2$ pumping system stops injecting, the injecting pressure inside the model drops to zero and the three-axial loading device is unloade, then the model is taken out of the thermo-controlled oven.

In step (IV), quantitative analysis is performed on the three-dimensional stress field obtained by the frozen experiment, namely, for the three-dimensional physical model obtained by the frozen experiment, the three-dimensional stress field distribution in each fracturing stage is obtained by slicing, two-dimensional photoelastic experiment and quantitative analysis of photoelastic fringe. Specifically, a slicer slices each of the three-dimensional physical models in different fracture states on which the cooling process has been performed, to obtain three orthogonal plane two-dimensional slices of each of the three-dimensional physical models. Preferably, three three-dimensional physical models on which the cooling process has been performed may be selected, and may be sliced along three orthogonal planes x-y, y-z, and z-x to obtain three orthogonal plane two-dimensional slices of the three-dimensional physical model and the slice has a thickness of 1 mm.

In step (V), a photoelastic stress test system performs a photoelastic analysis experiment on each of the orthogonal plane two-dimensional slices described above under the specific optical path, to obtain a photoelastic fringe pattern of each slice. In a specific practical application, the three orthogonal plane two-dimensional slices may be first smoothed and polished to make them meet the experimental requirements, and then the smoothed and polished orthogonal plane two-dimensional slices are subjected to two-dimensional photoelastic experiment to obtain a stress fringe distribution.

In step (VI), a computer obtains a distribution of a principal stress direction angle $\theta_u$ in a full field through a four-step color phase shift method, $$\theta = \frac{\pi}{8} - 0.25\tan\left[\frac{I_1 - I_3}{I_2 - I_4}\right],$$

and $\sin\delta \neq 0$, where $I_i$ is an intensity of an incident light.

An isochromatics phase diagram $\delta_u$ is obtained through an improved six-step phase shift method, $$\delta = \tan^{-1}\left[\frac{(I_5 - I_3)\sin2\theta_u + (I_4 - I_6)\cos2\theta_u}{I_1 - I_2}\right]$$

where $\begin{cases} I_5 - I_3 = -I_a\sin\delta\sin2\theta, \\ I_4 - I_6 = -I_a\sin\delta\cos2\theta, \\ I_1 - I_2 = -I_a\cos\delta \end{cases}$ $I_a$ is a modulation light intensity.

A distribution of the stress field of the full field is calculated, $$\tau = \frac{\delta_u f_\sigma}{4\pi h}\sin2\theta_u, (\sigma_x)_j = (\sigma_x)_i - \int_i^j \frac{\partial\tau_{xy}}{\partial y}dx$$

where $f_\sigma$ is a fringe value of the model, and h is a thickness of the model.

Stress components in three orthogonal planes are synthesized to obtain the distribution of the three-dimensional stress field at each point in the three-dimensional physical model.

Figure 2:
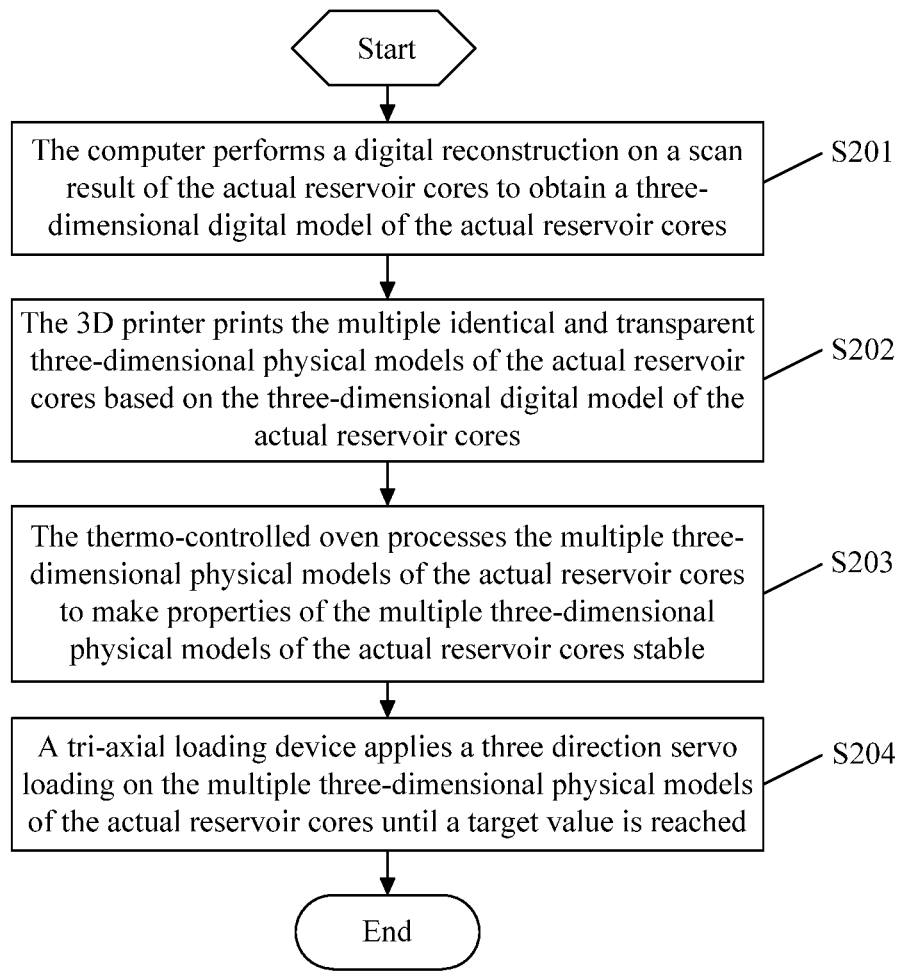
FIG. 2 is a flowchart of a method for measuring a stress field evolution during a $CO_2$ fracturing process according to another embodiment of the present disclosure.

A method for processing a three-dimensional physical model before performing a $CO_2$ fracturing is provided according to another embodiment of the present disclosure. Based on the embodiments above, before step S101 of FIG. 1, referring to FIG. 2, the method further includes the following steps S201 to S204.

In step S201, the computer performs a digital reconstruction on a scan result of the actual reservoir cores to obtain a three-dimensional digital model of the actual reservoir cores.

In step S202, the 3D printer prints the multiple identical and transparent three-dimensional physical models of the actual reservoir cores based on the three-dimensional digital model of the actual reservoir cores.

Specifically, a substrate portion may be printed using the Vero Clear material having photoelastic properties, and a pore or fracture portion may be printed using the Fullcure 705 material.

In step S203, the thermo-controlled oven processes the multiple three-dimensional physical models of the actual reservoir cores to make properties of the multiple three-dimensional physical models of the actual reservoir cores stable.

Preferably, the thermo-controlled oven slowly heats the multiple three-dimensional physical models of the actual reservoir cores to 60° C., and the thermo-controlled oven maintains the temperature for one hour to make the properties of the multiple the three-dimensional physical models of the actual reservoir cores stable.

In step S204, a tri-axial loading device applies a three direction servo loading on the multiple three-dimensional physical models of the actual reservoir cores until a target value is reached.

After the preset freezing temperature is reached, the temperature is kept constant for one hour to ensure that a uniform freezing temperature is reached inside and outside the three-dimensional physical model. And then three direction servo loading is applied on the three-dimensional physical model to reach a target value by step S204.

The target value may depend on the specific application environment, which is not limited herein, and all the target values fall within the protection scope of the present disclosure.

Figure 3:
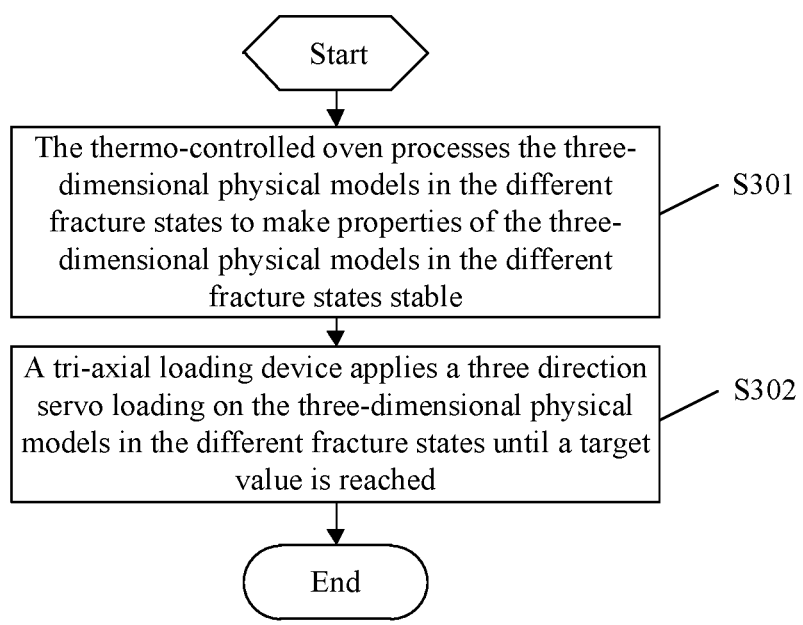
FIG. 3 is a flowchart of a method for measuring a stress field evolution during a $CO_2$ fracturing process according to another embodiment of the present disclosure.

In addition, when a stress frozen experiment is performed on the three-dimensional physical model in the different fracture states, it is required to ensure that when the specimen reaches the freezing temperature, the external stress applied to the specimen is kept constant, and the specimen is in the linear elastic stage while the specimen cannot be damaged. Therefore, preferably, before step S104 of FIG. 1, referring to FIG. 3, the method further includes the following steps S301 to S302.

In step S301, the thermo-controlled oven processes the three-dimensional physical models in the different fracture states to make properties of the three-dimensional physical models in the different fracture states stable.

Preferably, the thermo-controlled oven slowly heats the three-dimensional physical models in the different fracture states to 60° C., and maintains the temperature for one hour to make the properties of the three-dimensional physical models in the different fracture states stable.

In step S302, a tri-axial loading device applies a three direction servo loading on the three-dimensional physical models in the different fracture states until a target value is reached.

After the preset freezing temperature is reached, the temperature is kept constant for one hour to ensure that a uniform freezing temperature is reached inside and outside three-dimensional physical model and then three direction servo loadings are applied on the three-dimensional physical models until a preset target value is reached by step S204.

The target value may depend on the specific application environment, which is not limited herein, and all the target values fall within the protection scope of the present disclosure.

The thermo-controlled oven processes the above three-dimensional physical models. 60° C. is served as the freezing temperature of each of the three-dimensional physical models. In practice, other temperatures may also be available, which are not limited herein. For the specific values, reference may be made to the thermo-optic curve of the three-dimensional physical model as shown in FIG. 4, and the thermo-optic curve is generally obtained by recording the change in the number of fringe order of the circular-disk under diametrical compression at different temperatures.

Specifically, the photoelastic material Vero Clear used in the experiment may be tested in detail by designing a reflective photoelastic experiment at different temperature points. The disc specimen of ϕ50×8 mm is printed by 3D printing technology. To eliminate the reflection in the experiment, one side of the disk specimen may be sprayed first. Then, the self-designed connecting rod device is used to diametrically load the disc in a thermo-controlled oven, and the thermo-controlled oven can be set in terms of different temperature control curve programs and has a shooting window. In the experiment, the temperature is raised to the target temperature at a speed of 10° C./h, and the target temperature is maintained for 15 minutes. The number of fringe order at the center of the disc is recorded by a camera, and a thermo-optic curve of Vero Clear as shown in FIG. 4 is drawn according to the fringe data measured at different temperature points.

Then, in the thermo-optic curve, each temperature at a transition state stage is selected as the target temperature, and the physical and mechanical properties of the printed model at the target temperature are tested. In this embodiment, combining the variation trend of different temperature points in the thermo-optic curve and the physical and mechanical properties of the material, the transition state temperature of 60° C. is selected as the freezing temperature. In practice, other temperatures may also be selected, which are not limited herein, and all other temperatures are within the protection scope of the present disclosure.

Figure 5:
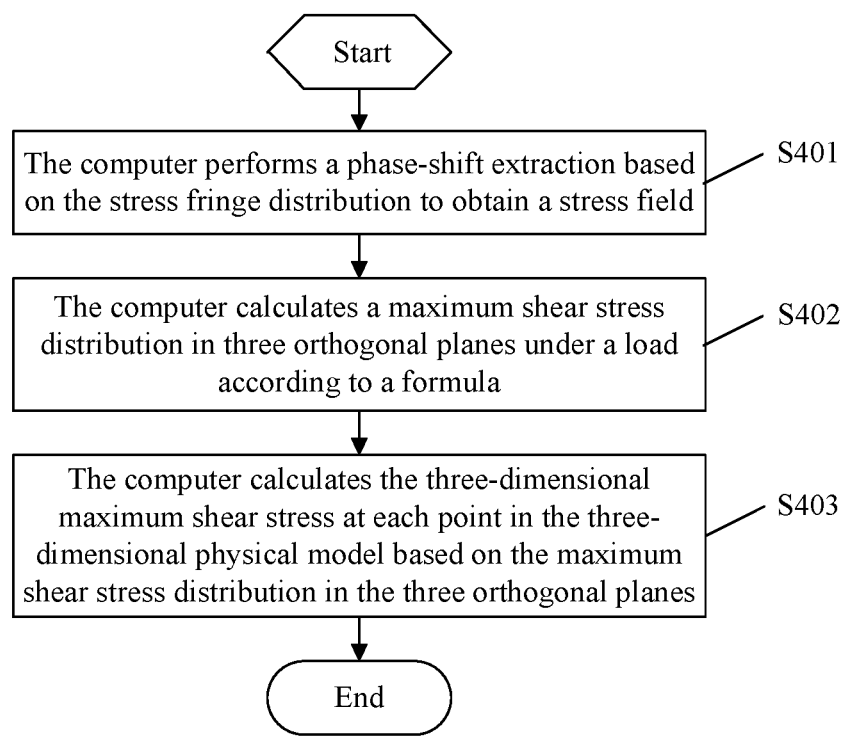
FIG. 5 is a flowchart of a method for measuring a stress field evolution during a $CO_2$ fracturing process according to another embodiment of the present disclosure.

A method for converting a slice fringe pattern into a three-dimensional stress field is provided according to another embodiment of the present disclosure. Based on the above embodiments and FIG. 1 to FIG. 3, step S107 as shown in FIG. 5 includes steps S401 to S403.

In step S401, the computer performs a phase-shifting extraction based on the stress fringe distribution to obtain a stress field.

In step S402, the computer calculates a maximum shear stress distribution $(\tau_{max})_{xy}$, $(\tau_{max})_{yz}$ and $(\tau_{max})_{zx}$ in three orthogonal planes under a load according to a formula $\tau_{max} = \sqrt{(\tau_{max})_{xy}^2 + (\tau_{max})_{yz}^2 + (\tau_{max})_{zx}^2}$; and In step S403, the computer calculates the three-dimensional maximum shear stress at each point in the three-dimensional physical model based on the maximum shear stress distribution $(\tau_{max})_{xy}$, $(\tau_{max})_{yz}$ and $(\tau_{max})_{zx}$ in the three orthogonal planes.

Unlike the existing method for displaying the evolution in the fracturing stress field by using a numerical simulation, the method for measuring the stress field evolution during the $CO_2$ fracturing process provided by the embodiment is adapted to not only transparently display the spatial distribution and propagation morphology of internal fracture of three-dimensional physical models in the fracturing process, but also obtain internal three-dimensional stress phase diagram in a fracture propagation process by integration of a CT scanning, a digital reconstruction, a 3D printing, a $CO_2$ fracturing experiments, a stress freezing and a photoelastic measurement techniques, thereby realizing transparent display and quantitative characterization of the three-dimensional stress field and its evolution law of a solid matter in the $CO_2$ fracturing process. In addition, the display and characterization above can be realized by using multiple identical and transparent three-dimensional physical models, ensuring the accuracy and reliability of the measurement results, whereby the problem existed in the existing numerical simulation method that the accuracy and reliability cannot be ensured due to low computational precision can be solved.

The embodiments of the present disclosure are described in a progressive manner. Each embodiment mainly focuses on an aspect different from other embodiments, and reference can be made to these similar parts among the embodiments. For the devices provided in the embodiments, the description thereof is simple since they correspond to the methods provided in the embodiments, and for relevant matters references may be made to the description for the method embodiment.

For the above-described various embodiments of the method, for the sake of simplicity, the method is described as a combination of a series of actions, those skilled in the art should recognize that the present disclosure is not limited by the sequence of actions described above, nor by the sequence of "I, II, III, etc." or "1, 2, 3, etc, this is because certain steps may be carried out in other order or at the same time according to the present disclosure. It is to be understood by those skilled in the art that the embodiments described in the specification are preferred embodiments and involved actions and modules are not necessary for the present disclosure.

It should be noted that, the relationship terms such as "first", "second" and the like are only used herein to distinguish one entity or an operation from another, rather than to necessitate or imply that an actual relationship or order exists between the entities or operations. Moreover, terms "comprising", "including", or any other variant thereof are intended to encompass a non-exclusive inclusion such that processes, methods, articles, or devices that include a series of elements include not only those elements but also those that are not explicitly listed or other elements that are inherent to such processes, methods, articles, or devices. Without further limitation, the element limited by the statement "comprising one . . . " do not exclude that there are other elements in the process, method, article, or device that includes said element.

The above description is merely a preferred embodiment of the present disclosure and does not limit the present disclosure in any form. Although the present disclosure is disclosed with the above preferred embodiments, the above preferred embodiments are not intended to limit the present disclosure. Many variations and modifications may be made to the technical solution of the present disclosure, or equivalent embodiments may be modified from the technical solution of the present disclosure by those skilled in the art based on the methods and the technical contents disclosed above without departing from the scope of the present disclosure. Therefore, all contents that do not depart from the technical solution of the present disclosure, and any simple alteration, equivalent variation and modification made to the embodiments based on the technical substance of the present disclosure should all fall in the scope of protection of the present disclosure.

The invention claimed is:

1. A method for measuring a stress field evolution during a $CO_2$ fracturing process, comprising:
performing, by a $CO_2$ pumping system, a $CO_2$ fracturing experiment on a plurality of identical and transparent three-dimensional physical models of actual reservoir cores;
performing, by a computer, a digital reconstruction on a CT scan result of the three-dimensional physical models on which the $CO_2$ fracturing experiment has been performed, to obtain a three-dimensional digital model with a complete fracture network, and clipping, by the computer, different fracture states in the three-dimensional digital model with the complete fracture network to generate three-dimensional digital models in different fracture states;
printing, by a 3D printer, a plurality of three-dimensional physical models in the different fracture states based on the three-dimensional digital models in the different fracture states;
performing, by the $CO_2$ pumping system, a $CO_2$ fracturing experiment on each of the three-dimensional physical models in the different fracture states under a target pressure corresponding to the three-dimensional physical model;
performing, by a thermo-controlled oven, a cooling process on each of the three-dimensional physical models on which the $CO_2$ fracturing experiment has been performed under the target pressure corresponding to the three-dimensional physical model;
slicing, by a slicer, each of the three-dimensional physical models on which the cooling process has been performed, to obtain three orthogonal plane two-dimensional slices of each of the three-dimensional physical models; and
processing, by the computer, a stress fringe distribution to obtain a three-dimensional maximum shear stress at each point in each of the three-dimensional physical models, wherein the stress fringe distribution is obtained by performing a two-dimensional photoelastic experiment on the three orthogonal plane two-dimensional slices that meet experimental requirements.

2. The method for measuring the stress field evolution during the $CO_2$ fracturing process according to claim 1, wherein the different fracture states comprise a state before fracture initiation, a state that a fracture propagates to a preset length, and a state that a fracture arrests; and
the clipping different fracture states in the three-dimensional digital model with the complete fracture network to generate three-dimensional digital models in different fracture states comprises:
performing a region threshold segmentation, a clipping and a reconstruction on an image of the CT scan result by an image processing technology to obtain a three-dimensional digital model in the state that a fracture propagates to a preset length.

3. The method for measuring the stress field evolution during the $CO_2$ fracturing process according to claim 2, wherein the performing, by the $CO_2$ pumping system, a $CO_2$ fracturing experiment on each of the three-dimensional physical models in the different fracture states under a target pressure corresponding to the three-dimensional physical model comprises:
injecting, by the $CO_2$ pumping system, a supercritical $CO_2$ into a three-dimensional physical model in the state before fracture initiation, and stopping injecting the supercritical $CO_2$ and maintaining a current injecting pressure when the injecting pressure is lower than a breakdown pressure by a preset pressure difference; and
injecting, by the $CO_2$ pumping system, a supercritical $CO_2$ into a three-dimensional physical model in the state that a fracture propagates to a preset length, and stopping injecting the supercritical $CO_2$ and maintaining a current injecting pressure when the injecting pressure is lower than a pressure at which a current fracture is formed by a preset pressure difference.

4. The method for measuring the stress field evolution during the $CO_2$ fracturing process according to claim 1, wherein before the performing, by a $CO_2$ pumping system, a $CO_2$ fracturing experiment on a plurality of identical and transparent three-dimensional physical models of actual reservoir cores, the method further comprises:
performing, by the computer, a digital reconstruction on a scan result of the actual reservoir cores to obtain a three-dimensional digital model of the actual reservoir cores;
printing, by the 3D printer, the plurality of identical and transparent three-dimensional physical models of the actual reservoir cores based on the three-dimensional digital model of the actual reservoir cores;
processing, by the thermo-controlled oven, the plurality of three-dimensional physical models of the actual reservoir cores to make properties of the plurality of three-dimensional physical models of the actual reservoir cores stable; and applying, by a tri-axial loading device, a three direction servo loading on the plurality of three-dimensional physical models of the actual reservoir cores until a target value is reached.

5. The method for measuring the stress field evolution during the $CO_2$ fracturing process according to claim 1, wherein before performing, by the $CO_2$ pumping system, a $CO_2$ fracturing experiment on each of the three-dimensional physical models in the different fracture states under a target pressure corresponding to the three-dimensional physical model, the method further comprises:

processing, by the thermo-controlled oven, the three-dimensional physical models in the different fracture states to make properties of the three-dimensional physical models in the different fracture states stable; and applying, by a tri-axial loading device, a three direction servo loading on the three-dimensional physical models in the different fracture states until a target value is reached.

6. The method for measuring the stress field evolution during the $CO_2$ fracturing process according to claim 4, wherein the processing, by a thermo-controlled oven, the plurality of three-dimensional physical models of the actual reservoir cores to make properties of the plurality of three-dimensional physical models of the actual reservoir cores stable comprises:

slowly heating, by the thermo-controlled oven, the plurality of three-dimensional physical models of the actual reservoir cores to 60° C., and maintaining, by the thermo-controlled oven, the temperature for one hour to make the properties of the plurality of the three-dimensional physical models of the actual reservoir cores stable.

7. The method for measuring the stress field evolution during the $CO_2$ fracturing process according to claim 5, wherein the processing, by a thermo-controlled oven, the three-dimensional physical models in the different fracture states to make properties of the three-dimensional physical models in the different fracture states stable comprises:

slowly heating, by the thermo-controlled oven, the three-dimensional physical models in the different fracture states to 60° C., and maintaining, by the thermo-controlled oven, the temperature for one hour to make the properties of the three-dimensional physical models in the different fracture states stable.

8. The method for measuring the stress field evolution during the $CO_2$ fracturing process according to claim 1, wherein before the performing, by a $CO_2$ pumping system, a $CO_2$ fracturing experiment on three-dimensional physical models of actual reservoir cores, the method further comprises:

adjusting, by a temperature control system of the $CO_2$ pumping system, an injecting pressure and a temperature of $CO_2$.

9. The method for measuring the stress field evolution during the $CO_2$ fracturing process according to claim 1, wherein the performing, by a thermo-controlled oven, a cooling process on each of the three-dimensional physical models on which the $CO_2$ fracturing experiment has been performed under the target pressure corresponding to the three-dimensional physical model comprises:

setting a cooling speed of the thermo-controlled oven to be 2° C./h to make the temperate decline to an ambient temperate.

10. The method for measuring the stress field evolution during the $CO_2$ fracturing process according to claim 1, wherein the processing, by the computer, a stress fringe distribution to obtain a three-dimensional maximum shear stress at each point in each of the three-dimensional physical models comprises:

performing, by the computer, a phase-shifting extraction based on the stress fringe distribution to obtain a stress field;

calculating, by the computer, a maximum shear stress distribution $(\tau_{max})_{xy}$, $(\tau_{max})_{yz}$ and $(\tau_{max})_{zx}$ in three orthogonal planes under a load according to a formula $\tau_{max}=\sqrt{(\tau_{max})_{xy}^2+(\tau_{max})_{yz}^2+(\tau_{max})_{zx}^2}$; and calculating, by the computer, the three-dimensional maximum shear stress at each point in the three-dimensional physical model based on the maximum shear stress distribution $(\tau_{max})_{xy}$, $(\tau_{max})_{yz}$ and $(\tau_{max})_{zx}$ in the three orthogonal planes.

11. A measurement method for a three-dimensional stress field evolution during a $CO_2$ fracturing process, comprising:

obtaining transparent three-dimensional physical models of a complex rock mass by a 3D printing technology;

recording distribution characteristics of three-dimensional stress fields in different fracture states by a frozen experiment using the three-dimensional physical models; and quantitatively visualizing and analyzing a distribution of each of the three-dimensional stress fields based on a photoelastic experiment and a phase shift analysis, wherein the quantitatively visualizing and analyzing a distribution of each of the three-dimensional stress fields based on a photoelastic experiment and a phase shift analysis comprises:

slicing, by a slicer, each of the three-dimensional physical models in different fracture states on which a cooling process has been performed, to obtain three orthogonal plane two-dimensional slices of each of the three-dimensional physical models;

performing, by a photoelastic stress test system, a photoelastic analysis experiment on each of the orthogonal plane two-dimensional slices to obtain a photoelastic fringe pattern for each slice;

obtaining, by a computer, a distribution of a principal stress direction angle $\theta_u$ in a full field through a four-step color phase shift method, $$\theta = \frac{\pi}{8} - 0.25\tan\left[\frac{I_1 - I_3}{I_2 - I_4}\right],$$

and sin $\delta \neq 0$, where $I_i$ is an intensity of an incident light;

obtaining an isochromatics phase diagram $\delta_u$ through an improved six-step phase shift method, $$\delta = \tan^{-1}\left[\frac{(I_5 - I_3)\sin2\theta_u + (I_4 - I_6)\cos2\theta_u}{I_1 - I_2}\right]$$

where $\begin{cases} I_5 - I_3 = -I_a\sin\delta\sin2\theta, \\ I_4 - I_6 = -I_a\sin\delta\cos2\theta, \\ I_1 - I_2 = -I_a\cos\delta \end{cases}$ $I_a$ is a modulation light intensity; and
calculating a distribution of the stress field of the full field, $$\tau = \frac{\delta_u f_\sigma}{4\pi h}\sin 2\theta_u, \ (\sigma_x)_j = (\sigma_x)_i - \int_i^j \frac{\partial \tau_{xy}}{\partial y} dx$$

where $f_o$ is a fringe value of the model, and h is a thickness of the model;
synthesizing stress components in three orthogonal planes to obtain the distribution of the three-dimensional stress field at each point in the three-dimensional physical model.

\* \* \* \* \*